US011969317B2

(12) United States Patent
Locke et al.

(10) Patent No.: US 11,969,317 B2
(45) Date of Patent: Apr. 30, 2024

(54) WOUND DRESSING WITH WELDED ELASTIC STRUCTURE

(71) Applicants: KCI LICENSING, INC., San Antonio, TX (US); KCI USA, INC., San Antonio, TX (US); SYSTAGENIX WOUND MANAGEMENT, LIMITED, West Sussex (GB)

(72) Inventors: Christopher B. Locke, Bournemouth (GB); Benjamin A. Pratt, Poole (GB); Alexander Waite, Cowling (GB)

(73) Assignee: 3M Innovative Properties Company, Saint Paul, MN (US)

( * ) Notice: Subject to any disclaimer, the term of this patent is extended or adjusted under 35 U.S.C. 154(b) by 225 days.

(21) Appl. No.: 16/758,745

(22) PCT Filed: May 21, 2018

(86) PCT No.: PCT/US2018/033648
§ 371 (c)(1),
(2) Date: Apr. 23, 2020

(87) PCT Pub. No.: WO2019/083563
PCT Pub. Date: May 2, 2019

(65) Prior Publication Data
US 2021/0177662 A1 Jun. 17, 2021

Related U.S. Application Data

(60) Provisional application No. 62/577,556, filed on Oct. 26, 2017.

(51) Int. Cl.
A61F 13/02 (2006.01)
A61F 13/0203 (2024.01)
(Continued)

(52) U.S. Cl.
CPC ...... *A61F 13/0213* (2013.01); *A61F 13/0206* (2013.01); *A61L 15/225* (2013.01);
(Continued)

(58) Field of Classification Search
CPC .............. A61F 13/0213; A61F 13/0206; A61F 2013/00131; A61L 15/44; A61L 15/225; A61L 15/425
See application file for complete search history.

(56) References Cited

U.S. PATENT DOCUMENTS 1,355,846 A * 10/1920 Rannells ............. A61F 13/2048
604/286
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report and Written Opinion in International Application No. PCT/US2018/033648, dated Sep. 12, 2018.
(Continued)

Primary Examiner — Guy K Townsend

(57) ABSTRACT

A wound dressing includes an inelastic absorbent layer, an elastic film, and a plurality of welds. The inelastic absorbent layer is configured to absorb wound fluid and has a first side and a second, wound-facing side. The elastic film is configured to elastically stretch when a stretching force is applied to the wound dressing and elastically recover when the stretching force is removed. The plurality of welds fix the elastic film to the first side of the inelastic absorbent layer such that the elastic film and the inelastic absorbent layer elastically stretch and elastically recover as a unit.

23 Claims, 5 Drawing Sheets

(51) Int. Cl.
*A61F 13/0206* (2024.01)
*A61L 15/22* (2006.01)
*A61L 15/42* (2006.01)
*A61F 13/00* (2006.01)
*A61L 15/44* (2006.01)

(52) U.S. Cl.
CPC ... *A61L 15/425* (2013.01); *A61F 2013/00131* (2013.01); *A61L 15/44* (2013.01)

(56) References Cited

U.S. PATENT DOCUMENTS

| | | | |
|---|---|---|---|
| 2,632,443 A * | 3/1953 | Lesher | A61F 13/01021 604/377 |
| 2,682,873 A * | 7/1954 | Evans | A61F 13/01029 604/377 |
| 2,910,763 A * | 11/1959 | Lauterbach | D04H 3/013 26/18.5 |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A * | 1/1981 | Lloyd | A61L 15/58 604/358 |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A * | 2/1983 | Errede | A61L 15/60 128/DIG. 21 |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A * | 8/1984 | Kashmer | A61M 1/784 604/320 |
| 4,475,909 A | 10/1984 | Eisenberg | |
| 4,480,638 A | 11/1984 | Schmid | |
| 4,525,166 A * | 6/1985 | Leclerc | A61M 1/68 604/313 |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A * | 2/1986 | Hasslinger | A61M 25/02 604/179 |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A * | 11/1990 | Zamierowski | A61M 1/85 604/305 |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A * | 12/1992 | Karami | A61F 13/0203 602/57 |
| 5,176,663 A * | 1/1993 | Svedman | A61F 13/0203 604/378 |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A * | 3/1994 | Komatsuzaki | A61F 13/00995 424/444 |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A * | 8/1995 | Todd | A61M 1/915 604/323 |
| 5,527,293 A | 6/1996 | Zamierowski | |
| 5,549,584 A * | 8/1996 | Gross | A61M 1/915 604/319 |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 8,258,367 B2 * | 9/2012 | Lawson | A61F 13/565 604/368 |
| 8,664,468 B2 * | 3/2014 | Lawson | A61F 13/5638 604/361 |
| 9,226,860 B2 * | 1/2016 | Lawson | A61F 13/5638 |
| 9,539,357 B2 * | 1/2017 | Ashraf | A61F 13/15617 |
| 10,064,767 B2 * | 9/2018 | Ferrer | A61F 13/51121 |
| 10,487,199 B2 * | 11/2019 | Maldonado | A61F 13/51462 |
| 11,351,063 B2 * | 6/2022 | Locke | A61M 1/915 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2007/0148433 A1 * | 6/2007 | Mallory | B32B 5/024 428/311.11 |
| 2008/0039759 A1 * | 2/2008 | Holm | A61F 13/0226 602/41 |
| 2008/0132864 A1 * | 6/2008 | Lawson | A61F 13/5638 604/367 |
| 2011/0196329 A1 * | 8/2011 | Eckstein | A61L 15/425 521/157 |
| 2015/0126949 A1 * | 5/2015 | Ashraf | D04H 1/4274 604/372 |
| 2015/0182387 A1 * | 7/2015 | Ferrer | A61F 13/51401 604/374 |
| 2015/0216733 A1 * | 8/2015 | Allen | A61M 1/90 604/319 |
| 2015/0376384 A1 * | 12/2015 | Maldonado | A61F 13/51462 604/367 |

(56) References Cited

U.S. PATENT DOCUMENTS

| | | | | |
|---|---|---|---|---|
| 2016/0058632 | A1* | 3/2016 | Lawson | A61F 13/537 604/385.01 |
| 2016/0279002 | A1* | 9/2016 | Sauer | A61F 13/51496 |
| 2021/0177662 | A1* | 6/2021 | Locke | A61L 15/425 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 0 737 461 A2 | 10/1996 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2008/019310 A1 | 2/2008 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al.; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp . 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

Detail A

Detail B

WOUND DRESSING WITH WELDED ELASTIC STRUCTURE

CROSS-REFERENCE TO RELATED APPLICATIONS

This Application claims the benefit of priority under 35 U.S.C. § 371 to international patent application number PCT/US2018/033648, filed on May 21, 2018, which claims the benefit of priority to U.S. Provisional Application No. 62/577,556, filed on Oct. 26, 2017, which are both incorporated herein by reference in their entirety.

BACKGROUND

The present disclosure relates generally to a wound dressing. The present disclosure relates more particularly to a wound dressing having a welded elastic structure to promote substantial elastic deformation and recovery.

Substantial elastic recovery may be particularly important for treating tissue in areas of relatively high articulation or flexure, such as proximal to shoulder, elbow, knee, ankle, or hip joints (particularly knee or elbow joints). It may be desirable for a wound dressing to be able to undergo significant local flexure and substantially retain its shape, and its contact with the tissue site, upon significant articulation. Maintaining shape or tissue contact can reduce the frequency of necessitated dressing changes, reduce tissue blistering from improper contact, increase exudate absorption, reduce healing time, increase patient comfort, or combinations thereof.

Some wound dressings include an absorbent layer made of a hydrofiber material. Hydrofibers are typically non-woven fibrous materials that include an entanglement of gelling (i.e., absorbent) fibers and non-gelling (i.e., reinforcing) fibers. When a hydrofiber material is stretched, the non-woven fibers pull apart from each other, resulting in plastic deformation. It can be challenging to make a hydrofiber material exhibit elastic recovery, especially when the wound dressing is wet as a result of absorbing wound fluid. For example, any bond of the hydrofiber material to other layers of wound dressing (e.g., a colloid/silicone interface, a backing layer, etc.) may fail when the wound dressing is wet, causing the hydrofiber material to become disassociated with the other layers of the wound dressing. It would be desirable to provide a wound dressing that overcomes these and other limitations of conventional wound dressings.

SUMMARY

One implementation of the present disclosure is a wound dressing including an inelastic absorbent layer, an elastic film, and a plurality of welds. The inelastic absorbent layer is configured to absorb wound fluid and has a first side and a second, wound-facing side. The elastic film is configured to elastically stretch when a stretching force is applied to the wound dressing and elastically recover when the stretching force is removed. The plurality of welds fix the elastic film to the first side of the inelastic absorbent layer such that the elastic film and the inelastic absorbent layer elastically stretch and elastically recover as a unit.

In some embodiments, the elastic film is configured to apply an elastic recovery force to the inelastic absorbent layer via the plurality of welds when the stretching force is removed. The elastic recovery force may cause the inelastic absorbent layer to elastically recover.

In some embodiments, the inelastic absorbent layer includes a nonwoven hydrofiber material. In some embodiments, the inelastic absorbent layer includes an entanglement of nonwoven fibers configured to separate from each other when the stretching force is applied. In some embodiments, the inelastic absorbent layer includes an antimicrobial agent. The antimicrobial agent can include antimicrobial silver, silver oxidized regenerated cellulose (ORC) (e.g., approximately 25 wt % ionically bound silver), polyhexamethylene biguanide (PHMB), or other antimicrobial agents, in various embodiments.

In some embodiments, the inelastic absorbent layer includes a plurality of cellulosic gelling fibers including at least one of carboxymethyl cellulose, carboxyethyl cellulose, hydroxyethyl cellulose, hydroxypropyl cellulose, hydroxypropylmethyl cellulose, or cellulose ethyl sulphonate. In some embodiments, the inelastic absorbent layer includes a plurality of reinforcing fibers including at least one of a polyurethane gel, an amide polymer, an olefin polymer, an ester polymer, or a modified acrylamide polymer.

In some embodiments, the inelastic absorbent layer includes a plurality of cellulosic gelling fibers and a plurality of reinforcing fibers. In some embodiments, the plurality of cellulosic gelling fibers form between 45% and 90% of the inelastic absorbent layer and the plurality of reinforcing fibers form between 10% and 55% of the inelastic absorbent layer.

In some embodiments, the elastic film includes at least one of a polyurethane film or a polyethylene film. In some embodiments, the elastic film has a thickness between 20 microns and 50 microns.

In some embodiments, the plurality of welds include radio frequency welds. In some embodiments, the plurality of welds are distributed across the elastic film and the inelastic absorbent layer. In some embodiments, the plurality of welds are distributed non-uniformly such that the plurality of welds cause the wound dressing to elastically stretch and elastically recover non-uniformly. In some embodiments, the plurality of welds comprise spot welds having diameters between 2 millimeters and 3 millimeters.

In some embodiments, the wound dressing includes a backing layer adhered to the elastic film layer opposite the inelastic absorbent layer. In some embodiments, the backing layer is substantially impermeable to liquid and substantially permeable to vapor. In some embodiments, the backing layer extends beyond a perimeter of the elastic film and the inelastic absorbent layer to provide an adhesive-coated margin configured to adhere the wound dressing to a surface.

In some embodiments, the wound dressing includes a non-adherent layer coupled to the second, wound-facing side of the inelastic absorbent layer. In some embodiments, the non-adherent layer includes a hydrophobic material. In some embodiments, the non-adherent layer includes at least one of an alkyl acrylate polymer, an alkacrylate polymer, or an alkyl alkacrylate polymer. In some embodiments, the non-adherent layer comprises a plurality of perforations distributed across a surface of the non-adherent layer.

In some embodiments, the elastic film is welded to the inelastic absorbent layer in a pre-stretched state such that the elastic film causes the inelastic absorbent layer to collapse when no external forces are applied to the wound dressing. In some embodiments, the elastic film is stretched by approximately 20% of its relaxed length when in the pre-stretched state.

In some embodiments, at least one of the elastic film or the inelastic absorbent layer includes a plurality of fenestrations configured to increase a distance that the wound dressing stretches per unit of the stretching force. In some embodiments, the plurality of fenestrations are distributed non-uniformly such that the plurality of fenestrations cause the wound dressing to elastically stretch and elastically recover non-uniformly.

In some embodiments, the wound dressing includes a length defining a size of the wound dressing along a first dimension and a width less than the length and defining a size of the wound dressing along a second dimension substantially perpendicular to the first dimension. In some embodiments, at least one of the elastic film or the inelastic absorbent layer includes a plurality of linear fenestrations aligned with the first dimension or the second dimension.

In some embodiments, the plurality of fenestrations are aligned with the first dimension and configured to increase a distance that the wound dressing stretches per unit of the stretching force when the stretching force is applied along the second dimension. In some embodiments, the plurality of fenestrations are aligned with the second dimension and configured to increase a distance that the wound dressing stretches per unit of the stretching force when the stretching force is applied along the first dimension.

Another implementation of the present disclosure is a wound dressing including a dressing layer and a backing layer. The dressing layer has a first side and a second, wound-facing side. The dressing layer includes an inelastic absorbent layer and an elastic film. The inelastic absorbent layer is configured to absorb wound fluid and has a first side and a second, wound-facing side. The elastic film is welded to the first side of the inelastic absorbent layer such that the dressing layer elastically stretches when a stretching force is applied to the wound dressing and elastically recovers when the stretching force is removed. The backing layer is adhered to the first side of the dressing layer.

In some embodiments, the elastic film is configured to apply an elastic recovery force to the inelastic absorbent layer when the stretching force is removed. The elastic recovery force may cause the dressing layer to elastically recover.

In some embodiments, the inelastic absorbent layer includes a nonwoven hydrofiber material. In some embodiments, the inelastic absorbent layer includes an entanglement of nonwoven fibers configured to separate from each other when the stretching force is applied. In some embodiments, the inelastic absorbent layer comprises an antimicrobial agent. The antimicrobial agent can include antimicrobial silver, silver oxidized regenerated cellulose (ORC) (e.g., approximately 25 wt % ionically bound silver), polyhexamethylene biguanide (PHMB), or other antimicrobial agents, in various embodiments.

In some embodiments, the inelastic absorbent layer includes a plurality of cellulosic gelling fibers including at least one of carboxymethyl cellulose, carboxylethyl cellulose, hydroxyethyl cellulose, hydroxypropyl cellulose, hydroxypropylmethyl cellulose, or cellulose ethyl sulphonate. In some embodiments, the inelastic absorbent layer includes a plurality of reinforcing fibers including at least one of a polyurethane gel, an amide polymer, an olefin polymer, an ester polymer, or a modified acrylamide polymer.

In some embodiments, the inelastic absorbent layer includes a plurality of cellulosic gelling fibers and a plurality of reinforcing fibers. In some embodiments, the plurality of cellulosic gelling fibers form between 45% and 90% of the inelastic absorbent layer and the plurality of reinforcing fibers form between 10% and 55% of the inelastic absorbent layer.

In some embodiments, the elastic film includes at least one of a polyurethane film or a polyethylene film. In some embodiments, the elastic film has a thickness between 20 microns and 50 microns.

In some embodiments, the elastic film is welded to the inelastic absorbent layer with radio frequency welds. In some embodiments, the elastic film is welded to the inelastic absorbent layer at a plurality of locations distributed across the dressing layer. In some embodiments, the plurality of locations are distributed non-uniformly such that the dressing layer elastically stretches and elastically recovers non-uniformly. In some embodiments, the elastic film is welded to the inelastic absorbent layer with spot welds having diameters between 2 millimeters and 3 millimeters.

In some embodiments, the backing layer is substantially impermeable to liquid and substantially permeable to vapor. In some embodiments, the backing layer extends beyond a perimeter of the dressing layer to provide an adhesive-coated margin configured to adhere the wound dressing to a surface.

In some embodiments, the dressing layer includes a non-adherent layer coupled to the second, wound-facing side of the inelastic absorbent layer. In some embodiments, the non-adherent layer includes a includes material. In some embodiments, the non-adherent layer includes at least one of an alkyl acrylate polymer, an alkacrylate polymer, or an alkyl alkacrylate polymer. In some embodiments, the non-adherent layer includes a plurality of perforations distributed across a surface of the non-adherent layer.

In some embodiments, the elastic film is welded to the inelastic absorbent layer in a pre-stretched state such that the elastic film causes the inelastic absorbent layer to collapse when no external forces are applied to the wound dressing. In some embodiments, the elastic film is stretched by approximately 20% of its relaxed length when in the pre-stretched state.

In some embodiments, at least one of the elastic film or the inelastic absorbent layer includes a plurality of fenestrations configured to increase a distance that the wound dressing stretches per unit of the stretching force. In some embodiments, the plurality of fenestrations are distributed non-uniformly such that the plurality of fenestrations cause the wound dressing to elastically stretch and elastically recover non-uniformly.

In some embodiments, the wound dressing includes a length defining a size of the wound dressing along a first dimension and a width less than the length and defining a size of the wound dressing along a second dimension substantially perpendicular to the first dimension. In some embodiments, at least one of the elastic film or the inelastic absorbent layer includes a plurality of linear fenestrations aligned with the first dimension or the second dimension.

In some embodiments, the plurality of fenestrations are aligned with the first dimension and configured to increase a distance that the wound dressing stretches per unit of the stretching force when the stretching force is applied along the second dimension. In some embodiments, the plurality of fenestrations are aligned with the second dimension and configured to increase a distance that the wound dressing stretches per unit of the stretching force when the stretching force is applied along the first dimension Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Referring generally to the FIGURES, a wound dressing with a welded elastic structure is shown, according to various exemplary embodiments. The wound dressing described herein can be configured to exhibit substantial elastic recovery under wound treatment conditions. Substantial elastic recovery may be particularly important for treating tissue in areas of relatively high articulation or flexure, such as proximal to shoulder, elbow, knee, ankle, or hip joints (particularly knee or elbow joints). It may be desirable for a wound dressing to be able to undergo significant local flexure and substantially retain its shape, and its contact with the tissue site, upon significant articulation. Maintaining shape or tissue contact can reduce the frequency of necessitated dressing changes, reduce tissue blistering from improper contact, increase exudate absorption, reduce healing time, increase patient comfort, or combinations thereof.

In some embodiments, the wound dressing includes a plurality of layers including at least an elastic film and an inelastic absorbent layer. The elastic film is welded to the inelastic absorbent layer to form a welded elastic structure. The inelastic absorbent layer is configured to absorb wound fluid and may include an entanglement of non-woven fibers. When subjected to a stretching force, the non-woven fibers of the absorbent layer may pull apart from each other, resulting in plastic deformation of the absorbent layer. The material of the absorbent layer is, in isolation, substantially inelastic, meaning that the absorbent layer does not return to its original shape after application of a stretching force. However, the elastic film is substantially elastic and configured to exhibit substantially elastic deformation and recovery.

Advantageously, the elastic film is welded to the absorbent layer, thereby fixing the elastic film to the absorbent layer and imbuing the elastic properties of the elastic film to the absorbent layer. For example, when a stretching force is applied to the wound dressing, both the elastic film and the absorbent layer may stretch together, as a unit. When the stretching force is removed, the elastic film may elastically recover and return to its original shape. Because the elastic film is secured to the absorbent layer, the elastic film may apply an elastic recovery force to the absorbent layer via the plurality of welds when returning to its original shape. The elastic recovery force causes the absorbent layer to elastically recover along with the elastic film. These and other features and advantages of the wound dressing are described in detail below.

Wound Dressing

Figure 1:
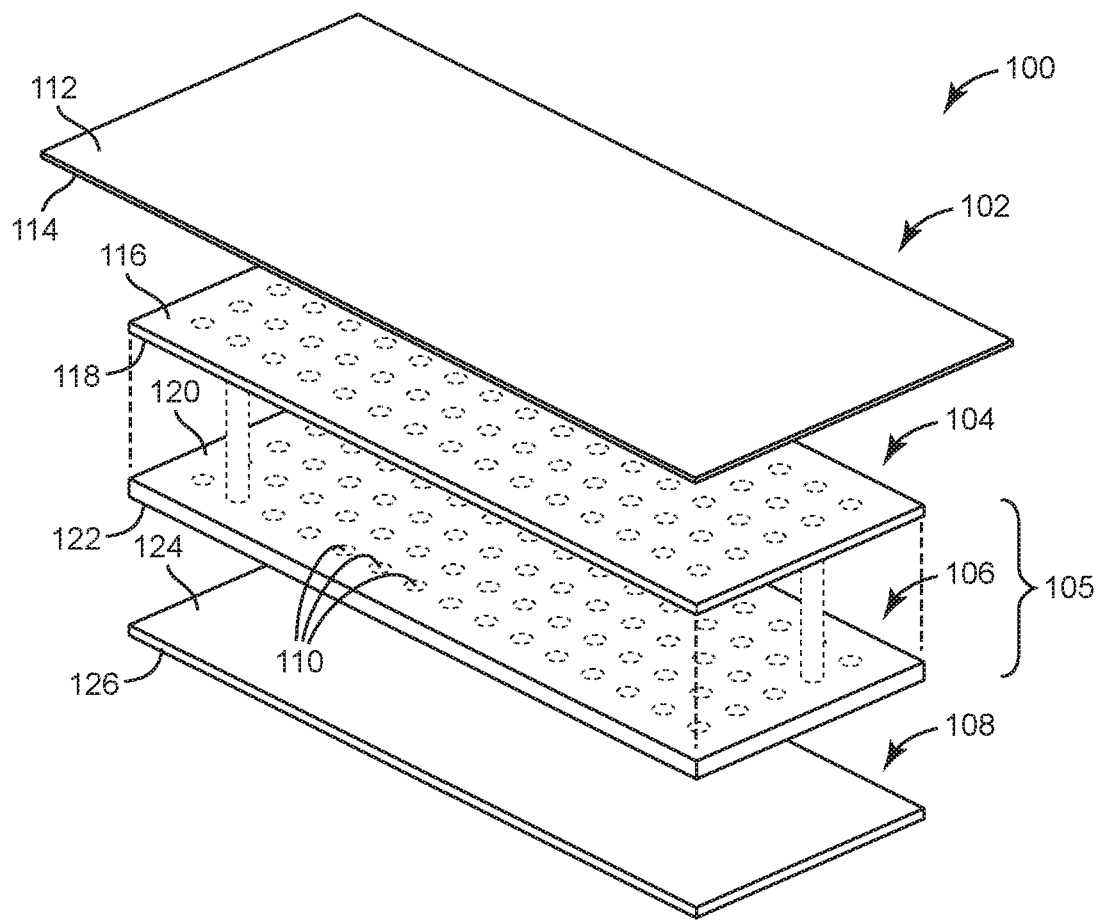
FIG. 1 is an exploded view of a wound dressing with a welded elastic structure, according to an exemplary embodiment.
Figure 2:
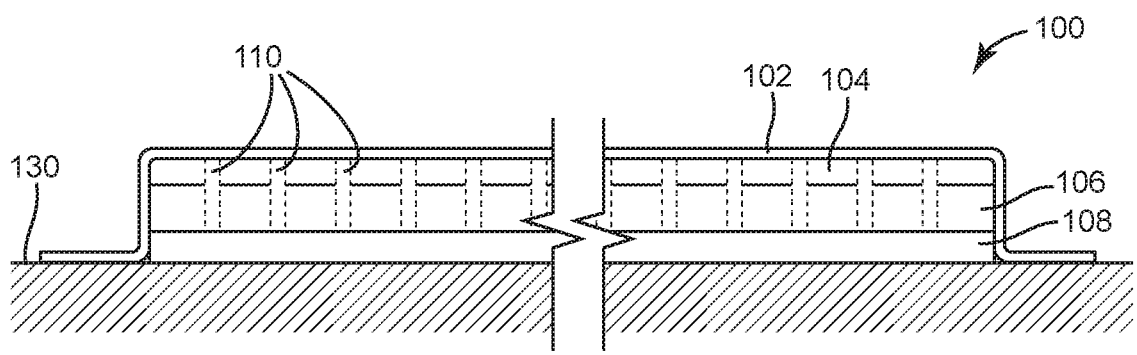
FIG. 2 is a cross-sectional view of the wound dressing of FIG. 1, according to an exemplary embodiment.

Referring now to FIGS. 1-2, a wound dressing 100 is shown, according to an exemplary embodiment. FIG. 1 is an exploded view of wound dressing 100, whereas FIG. 2 is a cross-sectional view of wound dressing 100 adhered to a surface 130. Wound dressing 100 is shown to include a plurality of layers including a backing layer 102, an elastic film 104, an inelastic absorbent layer 106, and a non-adherent layer 108. Elastic film 104 is welded to absorbent layer 106 via welds 110 to form a welded elastic dressing layer 105. In some embodiments, wound dressing 100 includes a removable cover sheet to cover absorbent layer 106 and/or non-adherent layer 108 before use. In some embodiments, one or more layers of wound dressing 100 can be omitted. Each layer of wound dressing 100 is described in detail below.

Wound dressing 100, as a whole, can be configured to exhibit substantially elastic recovery under tissue treatment conditions. Absorbent layer 106, in isolation, may be substantially inelastic and therefore may not exhibit elastic recovery. However, elastic film 104 is substantially elastic and fixed to absorbent layer via welds 110, thereby imbuing absorbent layer 106 with elastic properties. In this way, elastic film 104 enables absorbent layer 106, and thus wound dressing 100 as a whole, to exhibit substantially elastic recovery at tissue treatment conditions. This may be a desirable characteristic in combination with the ability to absorb wound fluid, especially when the ability to absorb wound fluid comes mainly from an absorbent layer 106 that does not exhibit substantial elastic recovery in isolation.

In various embodiments, wound dressing 100 can be formed as a substantially flat sheet for topical application to wounds or contoured for application to body surfaces having high curvature. The size of wound dressing 100 can vary depending on the size of the wound to be dressed. For example, it is contemplated that the size of wound dressing 100 can range from 1 cm$^2$ to 200 cm$^2$, and more preferably from 4 cm$^2$ to 100 cm$^2$. However, other shapes and sizes of wound dressing 100 are also possible depending on the intended use.

Backing Layer

Backing layer 102 is shown to include a first side 112 and a second, wound-facing side 114 opposite first side 112. When wound dressing 100 is applied to a wound, first side 112 faces away from the wound whereas second side 114 faces toward the wound. Backing layer 102 supports elastic film 104, absorbent layer 106, and non-adherent layer 108 and provides a barrier to passage of microorganisms through wound dressing 100. In some embodiments, backing layer 102 is a thin layer of polyurethane film. One example of a suitable material for backing layer 102 is the polyurethane film known as ESTANE 5714F. Other suitable polymers for forming backing layer 102 include poly alkoxyalkyl acrylates and methacrylates, such as those described in Great Britain Patent Application No. 1280631A filed Nov. 22, 2002, the entire disclosure of which is incorporated by reference herein. In some embodiments, backing layer 102 includes a continuous layer of a high-density blocked polyurethane foam that is predominantly closed-cell. Backing layer 102 may have a thickness in the range of 10 μm to 100 μm, preferably in the range of 50 μm to 70 μm. In some embodiments, backing layer 102 has a thickness of approximately 60 μm.

In some embodiments, backing layer 102 provides a barrier to microbes, a barrier to external contamination, and protection from physical trauma. For example, backing layer 102 may be constructed from a material that can reduce evaporative losses and provide a fluid seal between two components or two environments, such as between a therapeutic environment and a local external environment. Backing layer 102 may be formed of a suitable material, such as a polymer, for example, which may include an elastomeric film or membrane that can provide a seal at a tissue site. In some embodiments, backing layer 102 has a high moisture-vapor transmission rate (MVTR). For example, the MVTR of backing layer 102 may be at least 300 g/m$^2$ per twenty-four hours.

Backing layer 102 may be substantially impermeable to liquid and substantially permeable to moisture vapor. In other words, backing layer 102 may be permeable to water vapor, but not permeable to liquid water or wound exudate. This increases the total fluid handling capacity (TFHC) of wound dressing 100 while promoting a moist wound environment. In some embodiments, backing layer 102 is also impermeable to bacteria and other microorganisms. In some embodiments, backing layer 102 is configured to wick moisture from dressing layer 105 and distribute the moisture across first side 112.

Side 114 of backing layer 102 may be coated with an acrylic or other adhesive. The adhesive applied to side 114 ensures that wound dressing 100 adheres to surface 130 and that wound dressing 100 remains in place throughout the wear time. In some embodiments, the perimeter of backing layer 102 extends beyond (e.g., circumscribes) the perimeters of dressing layer 105 (i.e., elastic film 104 and absorbent layer 106) and non-adherent layer 108 to provide an adhesive-coated margin for adhering wound dressing 100 to the skin of a patient adjacent to the wound being treated, shown in FIG. 1 as surface 130. The adhesive-coated margin may extend around all sides of dressing layer 105 and non-adherent layer 108 such that wound dressing 100 is a so-called island dressing. In other embodiments, the adhesive-coated margin can be eliminated and wound dressing 100 can be adhered to surface 130 using other techniques.

In some embodiments, side 114 of backing layer 102 contacts side 116 of elastic film 104. Side 114 of backing layer 102 may be adhered to side 116 of elastic film 104 or may simply contact side 116 without the use of an adhesive. In some embodiments, the perimeter of non-adherent layer 108 extends beyond (i.e., circumscribes) the perimeter of dressing layer 105 to provide a margin around the perimeter of dressing layer 105. Side 114 of backing layer 102 may extend beyond the perimeter of dressing layer 105 to contact side 124 of non-adherent layer 108. Side 114 of backing layer 102 may adhere to side 124 of non-adherent layer 108 along the margin that extends beyond dressing layer 105. In this way, backing layer 102 and non-adherent layer 108 may form a closed pocket, sealing dressing layer 105 between backing layer 102 and non-adherent layer 108.

In some embodiments, the adhesive applied to side 114 of backing layer 102 is moisture vapor transmitting and/or patterned to allow passage of water vapor therethrough. The adhesive may include a continuous moisture vapor transmitting, pressure-sensitive adhesive layer of the type, conventionally used for island-type wound dressings (e.g., a polyurethane-based pressure sensitive adhesive). One example of an adhesive which can be used is a pressure sensitive adhesive based on acrylate ester copolymers, polyvinyl ethyl ether and polyurethane, as described in Great Britain Patent Application No. 1280631A. The basis weight of the adhesive may be 20 to 250 g/m$^2$, and more preferably 50 to 1.50 g/m$^2$.

Elastic Film

Elastic film 104 is shown to include a first side 116 and a second, wound-facing side 118 opposite first side 116. When wound dressing 100 is applied to a wound, first side 116 faces away from the wound whereas second side 118 faces toward the wound. Side 116 can be configured to contact side 114 of backing layer 102, whereas side 118 can be configured to contact side 120 of absorbent layer 106. Elastic film 104 is configured to elastically deform upon application of a stretching force to wound dressing 100. For example, elastic film 104 can elastically stretch when the stretching force is applied and can elastically recover when the stretching force is removed. In other words, elastic film 104 is configured to exhibit substantially elastic deformation and recovery.

In this context, a material that exhibits substantially elastic recovery under tissue treatment conditions is termed "elastic," whereas a material that does not exhibit substantially elastic recovery under tissue treatment conditions is termed "inelastic" or "not elastic." In some embodiments, wound dressing 100 or any layer(s) thereof, having a width and a length perpendicular to the width, may be considered elastic if it exhibits at most about 10% (advantageously about 5% or less or about 2% or less) permanent deformation (i.e., plastic deformation) when subjected to about 50% strain, relative to the length, for about 3 days at that strain level. In some embodiments, wound dressing 100 or any layer(s) thereof may be considered elastic if it exhibits at most about 5%, advantageously about 2% or less or about 1 or less, permanent deformation when subjected to about 25% strain, relative to the length, for about 24 hours at that strain level. In some embodiments, wound dressing 100 or any layer(s) thereof may be considered elastic if it exhibits at most about 1% (advantageously about 0%) permanent deformation when subjected to about 10% strain, relative to the length, for about 10 minutes at that strain level.

Even though particular values are specified with respect to the strain test, materials, layers, or compositions may be considered elastic if optionally tested with one or more parametric deviations. Such parametric deviations may include conducting the strain test at a greater strain than specified (e.g., between about 50% strain and about 100% strain, between about 25% strain and about 75% strain, or between about 10% strain and about 50% strain), conducting the strain test for a longer time than specified (e.g., between about 10 minutes and about 120 hours, between about 24 hours and about 96 hours, or between about 3 days and about 7 days), and/or conducting the strain test at a greater strain rate (e.g., between about 1% elongation per minute and about 600% elongation per minute, between about 10% elongation per minute and about 1200% elongation per minute, or between about 1% elongation per second and about 40% elongation per second).

Elastic film 104 may be a thin elastic film made of any of a variety of elastic materials. For example, elastic film 104 may be a polyurethane film, a polyethylene film, or other thin elastic film. In some embodiments, elastic film 104 has a thickness between 20 μm and 50 μm. In some embodiments, elastic film 104 has a thickness of approximately 30 μm. It is contemplated that the thickness of elastic film can vary based on the elasticity and/or strength of the material used to form elastic film 104. For example, elastic film 104 may be relatively thinner when the material used to form elastic film 104 has a high elasticity and/or strength, whereas elastic film 104 may be relatively thicker if the material used to form elastic film 104 has a lower elasticity and/or strength. The thickness of elastic film 104 can be selected to achieve a desired amount of force required to stretch elastic film 104.

In some embodiments, elastic film 101 is fenestrated in one or more directions to reduce the amount of force required to stretch elastic film 104. Several examples of fenestration patterns which can be used with elastic film 104 are described in greater detail with reference to FIGS. 8A-11B. In some embodiments, elastic film 104 is substantially impermeable to liquid and substantially permeable to moisture vapor. In other words, elastic film 104 may be permeable to water vapor, but not permeable to liquid water or wound exudate. Elastic film 104 can be configured to transmit water vapor at any of a variety of transmission rates based on the desired breathability and/or moisture vapor transmission rate (MVTR) for wound dressing 100.

Absorbent Layer

Absorbent layer 106 is configured to absorb wound fluid. Absorbent layer 106 is shown to include a first side 120 and a second, wound-facing side 122 opposite first side 120. When wound dressing 100 is applied to a wound, first side 120 faces away from the wound whereas second side 120 faces toward the wound. Side 120 can be configured to contact side 118 of elastic film 104, whereas side 122 can be configured to contact side 124 of non-adherent layer 108. For embodiments in which non-adherent layer 108 is omitted, side 122 of absorbent layer 106 can be configured to contact the wound directly.

Absorbent layer 106 may be made of a material that is inelastic (i.e., does not exhibit elastic deformation and recovery). For example, absorbent layer 106 may plastically deform when a stretching force is applied. However, absorbent layer 106 may not substantially recover or return to its original size or shape when the stretching force is removed. For purposes of this disclosure, a material may be considered "inelastic" if it deforms when a stretching force is applied, but recovers by less than a threshold amount when the stretching force is removed. The threshold amount may be defined as a percentage of the deformation (i.e., the difference between the stretched length and non-stretched length). For example, a perfectly elastic material recovers by 100%, meaning that 100% of the deformation is recovered and the perfectly elastic material returns to its original length. However, an inelastic material may recover by substantially less than 100% such that some or all of the deformation is retained as permanent deformation. For example, an inelastic material may recover less than 50% of the deformation (advantageously less than 25% or less than 10% of the deformation). In some embodiments, an inelastic material recovers less than 5% or less than 2% of the deformation. It should be noted that an inelastic material can recover a portion of the deformation and still be considered inelastic as long as the recovery amount does not exceed the threshold amount (e.g., 50% of the deformation, 25% of the deformation, 10% of the deformation, 5% of the deformation, 2% of the deformation, etc.). Accordingly, inelastic absorbent layer 106 may recover some, but not all, of the deformation when the stretching force is removed.

In some embodiments absorbent layer 106 exhibits different elastic properties when dry and wet. For example, absorbent layer 106 may be relatively more inelastic when absorbent layer 106 is wet and relatively less inelastic when absorbent layer 106 is dry. In other words, the amount of deformation that absorbent layer 106 recovers when wet may be less than the amount of deformation that absorbent layer 106 recovers when dry. For purposes of this disclosure, "inelastic absorbent" refers to an absorbent material that is inelastic when wet. The criteria for classifying absorbent layer 106 as inelastic when wet may be the same as previously described. For example, absorbent layer 106 may recover less than 50% of the deformation (advantageously less than 25% or less than 10% of the deformation) when wet. In some embodiments, absorbent layer 106 recovers less than 5% or less than 2% of the deformation when wet. However, absorbent layer 106 may be imbued with elastic properties when welded to elastic film 104, as described in greater detail below. In some embodiments, absorbent layer 106 includes a nonwoven hydrofiber material. For example, absorbent layer 106 may include comprises an entanglement of nonwoven fibers configured to separate from each other when the stretching force is applied.

Absorbent layer 106 may include a nonwoven material of predominantly nonwoven fibers. In some embodiments, absorbent layer 106 includes a combination of gelling (i.e., absorbent) fibers and non-gelling (i.e., reinforcing) fibers. The ratio of gelling fibers to non-gelling fibers can be varied to achieve different levels of force required to stretch absorbent layer 106. For example, the percentage of non-gelling reinforcing fibers may vary from 0% to 20%. The density and/or entanglement of fibers can be varied to adjust the amount of force required to stretch absorbent layer 106. In some embodiments, the density and/or entanglement of fibers within absorbent layer 106 is non-uniform such that some areas of absorbent layer 106 stretch more than others when a stretching force is applied to absorbent layer 106. Absorbent layer 106 may have a range of material weights (e.g., from 100 GSM to 250 GSM).

In some embodiments, absorbent layer 106 includes a combination of cellulosic fibers and reinforcing fibers. For example, absorbent layer 106 may include from about 45 parts to about 95 parts by weight of cellulosic fibers (e.g., cellulose ether) and from about 5 parts to about 55 parts by weight of reinforcing fibers. In particular embodiments, absorbent layer 106 may include from about 50 parts to about 95 parts by weight of cellulosic fibers, from about 45 parts to about 90 parts by weight of cellulosic fibers, from about 50 parts to about 90 parts by weight of cellulosic fibers, from about 60 parts to about 90 parts by weight of cellulosic fibers, from about 65 parts to about 85 parts by weight of cellulosic fibers, or from about 70 parts to about 90 parts by weight of cellulosic fibers. The cellulosic fibers may be composed of at least one of carboxymethyl cellulose (CMC), carboxylethyl cellulose, hydroxyethyl cellulose, hydroxypropyl cellulose, hydroxypropylmethyl cellulose, and cellulose ethyl sulphonate (CES) (particularly carboxymethyl cellulose).

Absorbent layer 106 may include from about 50 parts to about 5 parts by weight of reinforcing fibers, from about 55 parts to about 10 parts by weight of reinforcing fibers, from about 50 parts to about 10 parts by weight of reinforcing fibers, from about 45 parts to about 10 parts by weight of reinforcing fibers, from about 40 parts to about 10 parts by weight of reinforcing fibers, from about 35 parts to about 15 parts by weight of reinforcing fibers, from about 30 parts to about 10 parts by weight of reinforcing fibers, from about 30 parts to about 15 parts by weight of reinforcing fibers, or from about 25 parts to about 10 parts by weight of reinforcing fibers. The reinforcing fibers may be composed of at least one of non-gelling cellulose, a polyurethane gel, an amide polymer such as Nylon 6,6, an olefin polymer such as HDPE, an ester polymer such as PET, and/or a modified acrylamide polymer.

In some optional embodiments, biodegradable components may additionally be present in absorbent layer 106, for example in amounts from about 1 part to about 20 parts by weight (e.g., such as from about 1 part to about 20 parts by weight, from about 1 part to about 15 parts by weight or from about 1 part to about 10 parts by weight. The biodegradable components may be composed of, but not limited to, an alginic acid, an alginate salt, chitosan, chitin, a guar gum, a locust bean gum, a xanthan gum, a karaya gum, gelatin, pectin, a starch derivative, a glycosaminoglycan, a galactomannan, a chondroitin salt, heparin, a heparin salt, collagen, oxidized regenerated cellulose (ORC), hyaluronic acid, a hyaluronate salt, or a combination thereof.

In some embodiments, absorbent layer 106 is a single layer, whereas in other embodiments, absorbent layer 106 may include a multi-layer composite structure. For example, absorbent layer 106 may include at least two layers coupled to each other. Layers of the multi-layer composite structure may be coupled to each other using any appropriate technique. In some embodiments, a lamination process can be used to couple layers together, particularly where neither of the layers to be coupled are fibrous or only one of the two layers is fibrous. In some embodiments, an adhesive can be used to directly or indirectly couple layers together. In such embodiments, direct adhesion can be used particularly where neither of the layers to be coupled are fibrous, and indirect adhesion can be used particularly where at least one of the two layers is fibrous.

In some embodiments where at least one of the layers is fibrous, a needling apparatus, such as a needle loom machine, can be used to couple the fibrous layer to the other layer, whether fibrous or porous. Needling apparatuses may be used to knit together different types of fibrous materials, such as nonwoven materials. Typically, in needling apparatuses, a bottom layer can be coupled to a top layer by co-feeding the two layers through the apparatus to be simultaneously needled. By operation of such apparatuses, one or more barbed needles can be punctured into/through the fibrous material(s). Differences in strength or connectivity in coupling can arise in needling treatments from different numbers or arrays of barbed needles, from different barbed needle puncture speeds or frequencies, from different sizes of barbs or needles, from the like, or from some combination thereof. Repeated action of the barbed needles may effectively entangle or interweave the fibers of one or the layers with either the fibers or pore structure of the other layer, resulting in effective coupling.

In some embodiments, absorbent layer 106 includes multiple layers coupled by needling. For example, in a first step, coupling can be attained by co-feeding a top layer and a bottom layer through a needling apparatus to form a multi-layer composition. Then, by controlling the depth of needling, the top layer of the multi-layer composite, which represents the lower "layer" in this second step, can be coupled to a (fibrous) upper layer by co-feeding both to the needling apparatus and by ensuring that the needling depth does not exceed the thickness of the top layer of the composite, thereby forming a three-layer composite formed by two couplings via the needling apparatus. This process can be repeated with any desired number of layers to attain more highly layered composites. Additionally or alternatively, it is possible in multi-layered composites having at least two couplings for at least one of the couplings can be accomplished via needling, while at least one of the other couplings can be accomplished via a different coupling method, such as via lamination.

In some embodiments, absorbent layer 106 includes an antimicrobial agent or other active agents to promote effective wound healing. Non-limiting examples of such active materials may include antimicrobial silver, silver oxidized regenerated cellulose (ORC) (e.g., approximately 25 wt % ionically bound silver), polyhexamethylene biguanide (PHMB), non-steroidal anti-inflammatory drugs such as acetaminophen, steroids, anti-inflammatory cytokines, anesthetics, antimicrobial agents such as penicillin or streptomycin, antiseptics such as chlorhexidine, growth factors such as a fibroblast growth factor (FGF), a platelet derived growth factor (PDGF), or an epidermal growth factor (EGF), and other therapeutic agents, individually or in any combination. If present, such active materials may typically be included at any effective level that show therapeutic efficacy, while preferably not being at such a high level as to significantly counteract any critical or desired physical, chemical, or biological property of the dressing. Depending upon the therapeutic goal, any active material may be loaded at a level of from about 10 wppm to about 10 wt % of the layer in which it is present, for example, from about 50 wppm to about 5 wt % or from about 100 wppm to about 1 wt %.

Welds

Wound dressing 100 is shown to include a plurality of welds 110 that fix elastic film 104 to absorbent layer 106. In some embodiments, welds 110 fix side 118 of elastic film 104 to side 120 of absorbent layer 106. In various embodiments, welds 110 may be limited to the plane of contact between elastic film 104 and absorbent layer 106, or may extend into at least one of elastic film 104 and/or absorbent layer 106. For example, FIG. 2 shows welds 110 extending entirely through elastic film 104 and absorbent layer 106 (i.e., from side 116 of elastic film 104 to side 122 of absorbent layer 106). In some embodiments, welds 110 are radio frequency (RF) welds. However, it is contemplated that other types of welds 110 can also be used to fix elastic film 104 to absorbent layer 106.

Advantageously, welds 110 fix elastic film 104 to absorbent layer 106 such that elastic film 104 and absorbent layer 106 elastically deform (i.e., elastically stretch and elastically recover) as a unit. In some embodiments, the plurality of welds 110 are distributed uniformly across elastic film 104 and absorbent layer 106 (e.g., in a grid) to fix elastic film 104 to absorbent layer 106 at multiple locations evenly spaced across wound dressing 100. A uniform distribution of welds 110 may cause wound dressing 100 to elastically stretch and elastically recover uniformly (e.g., all parts of wound dressing 100 stretch substantially equally). In other embodiments, welds 110 can be distributed non-uniformly across wound dressing 100. A non-uniform distribution of welds 110 may cause wound dressing 100 to elastically stretch and elastically recover non-uniformly (e.g., some parts of wound dressing 100 stretch more than others).

Welds 110 can have any of a variety of shapes or sizes. For example, in some embodiments, welds 110 are spot welds having diameters between 2 mm and 3 mm. In other embodiments, welds 110 are bar welds, half-moons, or arcs spaced across elastic film 104 and absorbent layer 106. The size, shape, angle, and/or positioning of welds 110 can be selected to optimize strain distribution and achieve a desired ease or resistance of the expansion and collapse of elastic film 104 and absorbent layer 106. For example, the spacing between welds 110 can be increased in the central region of wound dressing 100 to cause wound dressing 100 to exhibit less strain in the central region. The spacing of welds 110 can be staggered such that an open area or rows between welds 110 in the central region of wound dressing is located between non-aligned welds 110. This may result in a higher required force to stretch the central region of wound dressing 100, which may be desirable for applications in which wound dressing 100 is placed over a wound on a highly flexible portion of a patient's body (e.g., knee, elbow, shoulder, etc.). In some embodiments, welds 110 can be arranged to form lettering or other symbols on wound dressing 100 (e.g., branding, directional instructions, etc.).

Advantageously, welds 110 secure elastic film 104 to absorbent layer 106 such that the elastic properties of elastic film 104 are imbued to absorbent layer 106. For example, when a stretching force is applied to wound dressing 100, both elastic film 104 and absorbent layer 106 may stretch together, as a unit. When the stretching force is removed, elastic film 104 may elastically recover and return to its original shape. Because elastic film 104 is secured to absorbent layer 106, elastic film 104 may apply an elastic recovery force to absorbent layer 106 via the plurality of welds 110 when returning to its original shape. The elastic recovery force causes absorbent layer 106 to elastically recover along with elastic film 104.

Non-Adherent Layer

In some embodiments, wound dressing 100 includes a non-adherent layer 108. Non-adherent layer 108 is shown to include a first side 124 and a second, wound-facing side 126 opposite first side 124. When wound dressing 100 is applied to a wound, first side 124 faces away from the wound whereas second side 126 faces toward the wound. Side 124 can be configured to contact side 122 of absorbent layer 106, whereas side 126 can be configured to contact the wound or tissue site over which wound dressing 100 is applied. Accordingly, non-adherent layer 108 may function as a contact layer providing an interface between wound dressing 100 and the wound or tissue site.

Non-adherent layer 108 may be advantageous in fibrinous situations to reduce potential adherence of absorbent layer 106 to the wound or tissue site, to enable fluid to be effectively drawn away from the wound via non-adherent layer 108, absorbent layer 106, or both. In some embodiments, non-adherent layer 108 is made of a hydrophobic material such as polyethylene (PE) or other hydrophobic polymers. The use of a hydrophobic material for non-adherent layer 108 may be particularly advantageous to prevent the attachment of bacteria to the wound or tissue site. In some embodiments, non-adherent layer 108 is perforated for increased fluid flow.

In various embodiments, non-adherent layer 108 may include at least one of an alkyl acrylate polymer (e.g., a methyl acrylate polymer, an ethyl acrylate polymer, or the like) an alkacrylate polymer (e.g., a methacrylate polymer, an ethacrylate polymer, or the like) and/or an alkyl alkacrylate polymer (e.g., a methyl methacrylate polymer, an ethyl methacrylate polymer, a methyl ethacrylate polymer, an ethyl ethacrylate polymer, or the like). Such (alk)acrylate polymers may be homopolymers but are more often copolymers, for example, with olefin comonomers. In some embodiments, non-adherent layer 108 includes anethylene-methyl acrylate copolymer, such as used in TIELLE dressings and SILVERCEL non-adherent dressings available from Systagenix Wound Management, Limited. In various embodiments, non-adherent layer 108 may include a silicone or polysiloxane polymer or copolymer.

In some embodiments, the perimeter of non-adherent layer 108 extends beyond the perimeter of dressing layer 105 such that a portion of non-adherent layer 108 contacts the wound-facing side 114 of backing layer 102. The perimeter of non-adherent layer 108 may contact the adhesive-coated margin of backing layer 102 to allow the perimeter of non-adherent layer 108 to adhere directly to backing layer 102, thereby forming a closed pocket within which dressing layer 105 is contained. In some embodiments, non-adherent layer 108 includes perforations through which backing layer 102 can contact surface 130 surrounding the wound. Alternatively, backing layer 102 may extend beyond a perimeter of non-adherent layer 108 to adhere to surface 130 around the outer perimeter of non-adherent layer 108.

Dressing Layer

Figure 3:
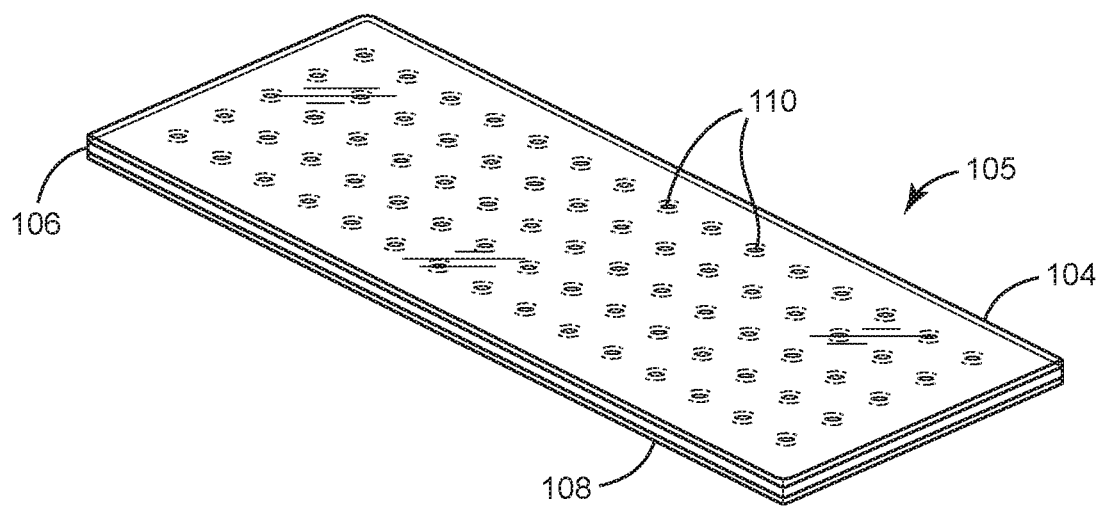
FIG. 3 is a top perspective view of a dressing layer of the wound dressing of FIG. 1, according to an exemplary embodiment.
Figure 4:
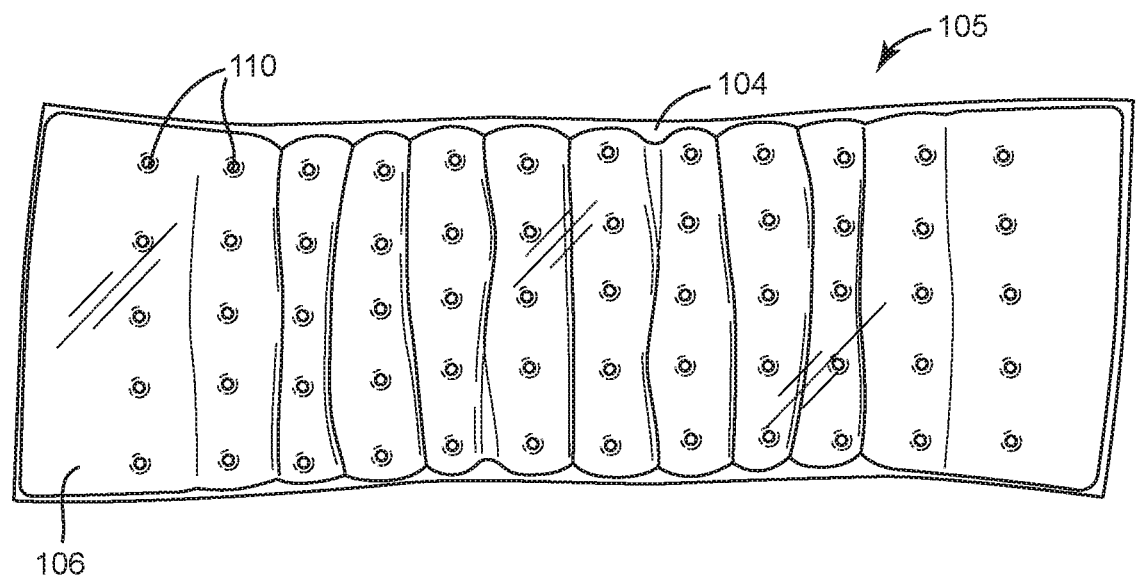
FIG. 4 is a top plan view of the dressing layer of FIG. 3, according to an exemplary embodiment.

Referring now to FIGS. 3-7, dressing layer 105 is shown, according to an exemplary embodiment. FIG. 3 is a top plan view of dressing layer 105, whereas FIG. 4 is a top perspective view of dressing layer 105. As described above, dressing layer 105 may include elastic film 104, absorbent layer 106, and a plurality of welds 110 that fix elastic film 104 to absorbent layer 106. In some embodiments, dressing layer 105 also includes non-adherent layer 108 coupled to the wound-facing side 122 of absorbent layer 106. As shown in FIG. 3, elastic film 104 and non-adherent layer 108 may encapsulate absorbent layer 106. For example, the perimeters of elastic film 104 and non-adherent layer 108 may be sealed together or adhered to each other to form a closed container within which absorbent layer 106 is located.

Figure 5:
FIG. 5 is a side elevation view illustrating a pre-stretching of an elastic film when forming the dressing layer of FIG. 3, according to an exemplary embodiment.
Figure 6:
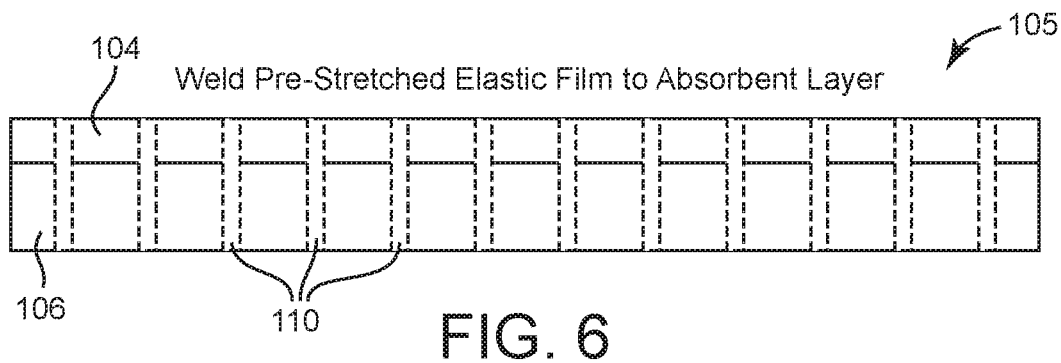
FIG. 6 is a side elevation view illustrating the pre-stretched elastic film welded to an absorbent layer to form the dressing layer of FIG. 3, according to an exemplary embodiment.

In some embodiments, dressing layer 105 is formed by pre-stretching elastic film 104 (as shown in FIG. 5) and welding the pre-stretched elastic film 104 to absorbent layer 106 (as shown in FIG. 6). The amount elastic film 104 is pre-stretched may depend on the elastic requirements of dressing layer 105 and the limitations of the materials used. In various embodiments, elastic film 104 can be stretched by an amount ranging from 5% to 40% of its original length, 15% to 30% of its original length, 20% to 25% of its original length, or preferably by approximately 20% of its original length prior to welding elastic film 104 to absorbent layer 106.

Figure 7:
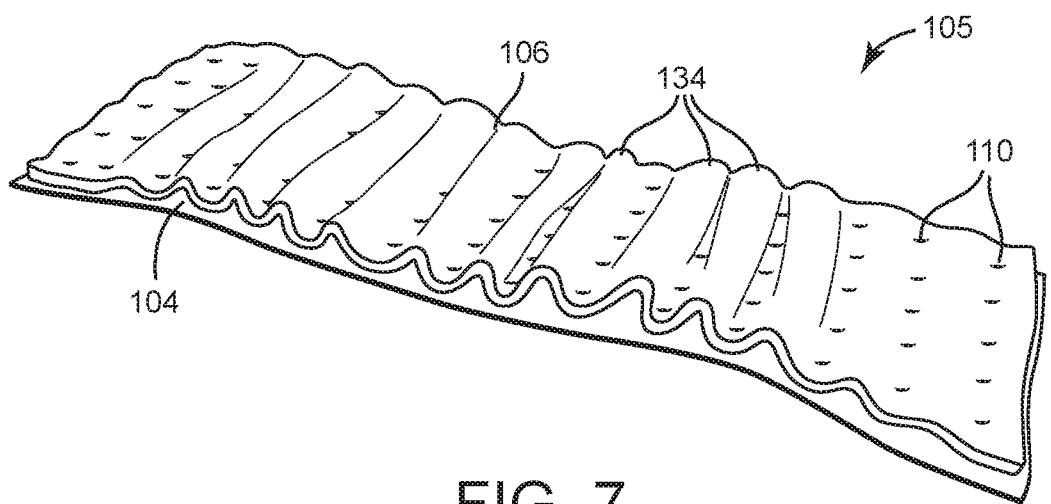
FIG. 7 is a top perspective view of the dressing layer of FIG. 3 after the pre-stretched elastic film is welded to the absorbent layer, according to an exemplary embodiment.

After welds 110 are added to secure the pre-stretched elastic film 104 to absorbent layer 106, the stretching force can be removed. In the absence of the stretching force, elastic film 104 may elastically recover, returning substantially to its original length. This causes absorbent layer 106 to compress (i.e., bunch up, collapse, etc.) longitudinally (as shown in FIG. 7), forming a plurality of waves or ridges 134 along the surface of absorbent layer 106. As an alternative to pre-stretching elastic film 104, absorbent layer 106 can be pre-compressed prior to adding welds 110. The resultant dressing layer 105 may be substantially the same as produced by the pre-stretching approach (i.e., absorbent layer 106 in a compressed state).

If a stretching force is subsequently applied to dressing layer 105, absorbent layer 106 can expand longitudinally (i.e., using the slack provided by ridges 134) without providing any resistance to stretching. The only resistance to stretching may come from elastic film 104, at least until absorbent layer 106 has completely flattened. Advantageously, this allows dressing layer 105 to be stretched by an amount equal to the pre-stretching of elastic film 104 (e.g., approximately 20%) with a relatively low stretching force (e.g., less than 2 N) since only elastic film 104 is providing resistance to stretching within the initial pre-stretching range. This also helps prevent the non-woven fibers of absorbent layer 106 from separating from each other since any stretching of absorbent layer 106 that occurs within the initial pre-stretching range is achieved by flattening ridges 134 rather than pulling apart the fibers of absorbent layer 106.

In some embodiments, elastic film 104 is welded to absorbent layer 106 without pre-stretching elastic film 104 and/or without pre-compressing absorbent layer 106. The welded assembly (i.e., dressing layer 105) can be stretched after the welding is complete. Such stretching may occur while wound dressing 100 is in use and/or during further fabrication of wound dressing 100. For example, dressing layer 105, as a whole, can be pre-stretched before dressing layer 105 is combined with backing layer 102 and/or non-adherent layer 108 to form wound dressing 100. The resultant wound dressing 100 may exhibit many of the same properties and advantages that result from pre-stretching elastic film 104, as previously described.

Fenestrations

Referring now to FIGS. 8A-11B, several patterns of welds 110 and fenestrations 132 which can be applied to wound dressing 100 are shown, according to various exemplary embodiments. Fenestrations 132 may be small cuts (e.g., slits, apertures, etc.) in one or more layers of wound dressing 100. In some embodiments, each of fenestrations 132 has a length of approximately 2 mm to 3 mm and a width of approximately 0.5 mm. However, other sizes and shapes of fenestrations 132 can be used in alternative embodiments. In various embodiments, fenestrations 132 can be added to absorbent layer 106, elastic film 104, non-adherent layer 108, and/or any combination thereof. Fenestrations 132 can be configured to increase the distance that wound dressing 100 stretches per unit of stretching force applied. In other words, fenestrations 132 may decrease the resistance to stretching provided by wound dressing 100.

The orientation of fenestrations 132 may imbue wound dressing 100 with varying levels of stretching resistance along different dimensions (e.g., length, width, etc.) based on the alignment of fenestrations 132 with the dimensions of wound dressing 100. In some embodiments, fenestrations 132 are substantially linear and oriented directionally such that fenestrations 132 reduce stretching resistance along only a single dimension of wound dressing 100. For example, wound dressing 100 may have a length (L) defining a size of wound dressing 100 along a first dimension (e.g., up and down in FIGS. 8A-11B) and a width (W) defining a size of wound dressing along a second dimension substantially perpendicular to the first dimension (e.g., left and right in FIGS. 8A-11B). In some embodiments, the width (W) is less than the length (L). Fenestrations 132 can be aligned with the width dimension or the length dimension to reduce the stretching resistance of wound dressing along either the width dimension or the length dimension.

Figure 8A:
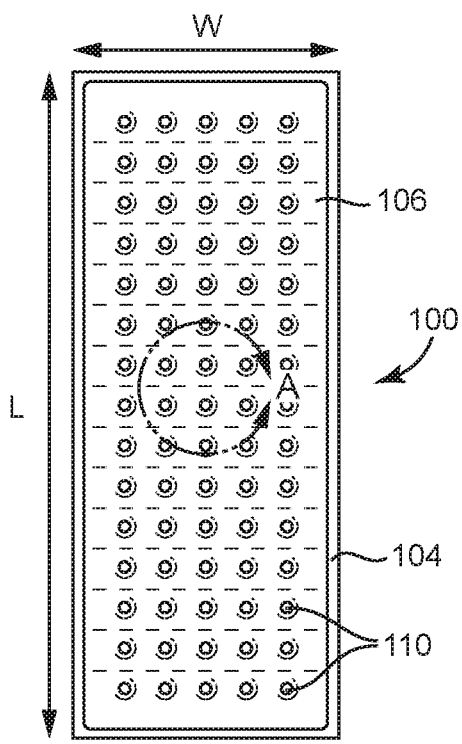
FIG. 8A is a top plan view of the wound dressing of FIG. 1 showing a plurality of fenestrations aligned with a width dimension of the wound dressing and a plurality of welds, according to an exemplary embodiment.
Figure 8B:
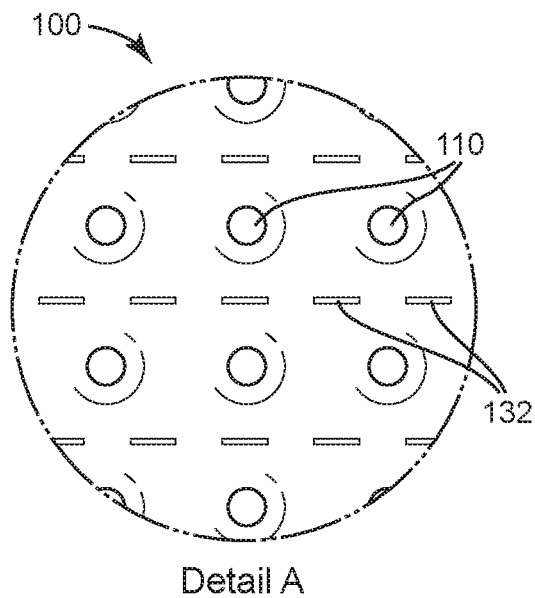
FIG. 8B is a detail view of a portion of FIG. 8A, according to an exemplary embodiment.

FIGS. 8A-8B illustrate an embodiment in which wound dressing 100 includes several rows of substantially linear fenestrations 132 aligned with the width (W) dimension of wound dressing 100. Each row of fenestrations 132 may include multiple fenestrations 132 arranged substantially linearly. Fenestrations 132 aligned with the width (W) dimension of wound dressing 100 may increase the distance that wound dressing 100 stretches along the length (L) dimension per unit of stretching force applied along the length (L) dimension. In other words, fenestrations 132 aligned with the width (W) dimension of wound dressing 100 may reduce the stretching resistance of wound dressing 100 along the length (L) dimension.

The embodiment shown in FIGS. 8A-8B also includes a substantially rectangular grid of welds 110 spaced uniformly along wound dressing 100. In some embodiments, the rows of linear fenestrations 132 are located between rows of welds 110. For example, rows of welds 110 and rows of fenestrations 132 may be arranged in an alternating pattern along the length (L) of wound dressing 100. In some embodiments, fenestrations 132 are spaced uniformly between welds 110. In other embodiments, fenestrations 132 may be spaced non-uniformly. A non-uniform spacing of fenestrations 132 can be used to achieve different levels of stretching resistance at different portions of wound dressing 100. For example, a region of wound dressing 100 with few fenestrations 132 may have a relatively high stretching resistance, whereas a region of wound dressing 100 with more fenestrations 132 may have a relatively lower stretching resistance.

Figure 9A:
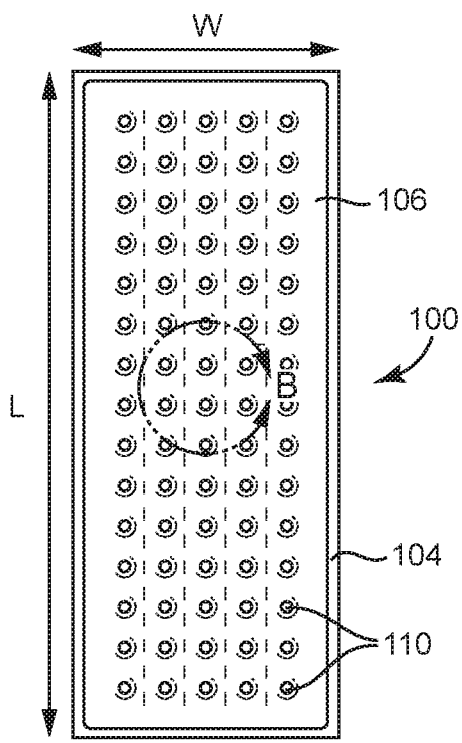
FIG. 9A is a top plan view of the wound dressing of FIG. 1 showing a plurality of fenestrations aligned with a length dimension of the wound dressing and a plurality of welds, according to an exemplary embodiment.
Figure 9B:
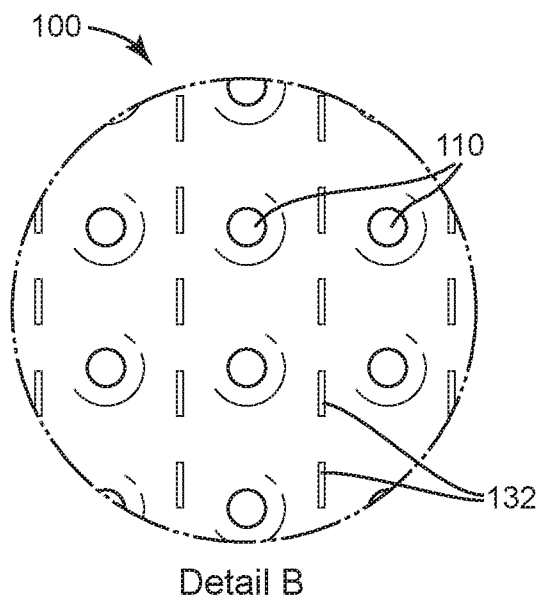
FIG. 9B is a detail view of a portion of FIG. 9A, according to an exemplary embodiment.

FIGS. 9A-9B illustrate an embodiment in which wound dressing 100 includes several columns of substantially linear fenestrations 132 aligned with the length (L) dimension of wound dressing 100. Each column of fenestrations 132 may include multiple fenestrations 132 arranged substantially linearly. Fenestrations 132 aligned with the length (L) dimension of wound dressing 100 may increase the distance that wound dressing 100 stretches along the width (W) dimension per unit of stretching force applied along the width (W) dimension. In other words, fenestrations 132 aligned with the length (L) dimension of wound dressing 100 may reduce the stretching resistance of wound dressing 100 along the width (W) dimension.

The embodiment shown in FIGS. 9A-9B also includes a substantially rectangular grid of welds 110 spaced uniformly along wound dressing 100. In some embodiments, the rows of linear fenestrations 132 are located between rows of welds 110. For example, rows of welds 110 and rows of fenestrations 132 may be arranged in an alternating pattern along the width (W) of wound dressing 100. As with the embodiment shown in FIGS. 8A-8B, fenestrations 132 can be spaced uniformly or non-uniformly between welds 110.

Figure 10A:
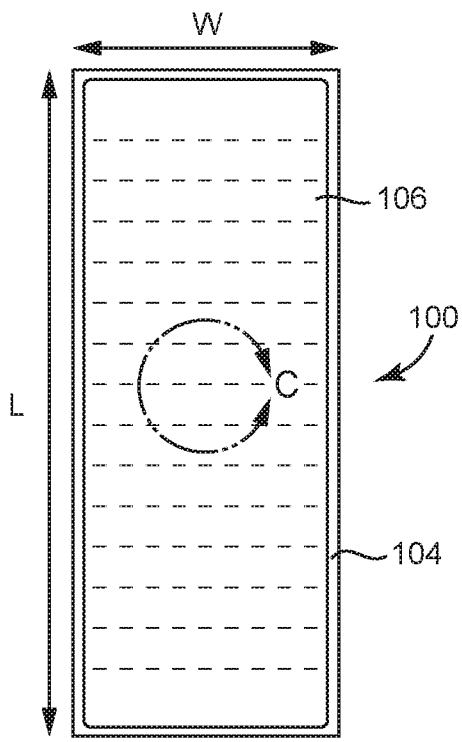
FIG. 10A is a top plan view of the wound dressing of FIG. 1 showing a plurality of fenestrations aligned with a width dimension of the wound dressing without the plurality of welds, according to an exemplary embodiment.
Figure 10B:
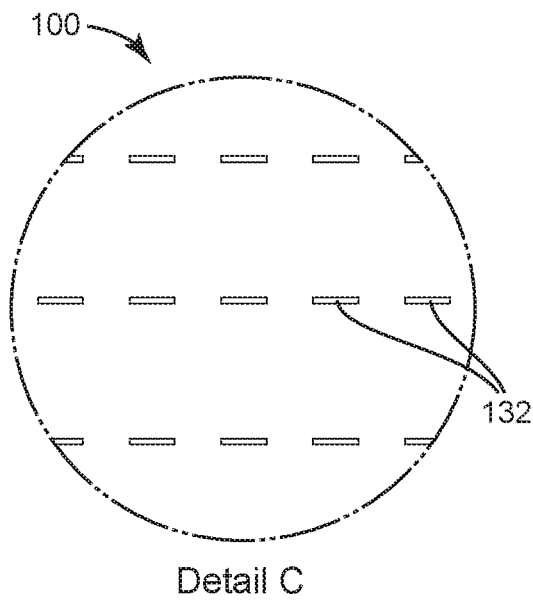
FIG. 10B is a detail view of a portion of FIG. 10A, according to an exemplary embodiment.

FIGS. 10A-10B illustrate another embodiment in which wound dressing 100 includes several rows of substantially linear fenestrations 132 aligned with the width (W) dimension of wound dressing 100, but does not include any welds 110. Each row of fenestrations 132 may include multiple fenestrations 132 arranged substantially linearly. Fenestrations 132 aligned with the width (W) dimension of wound dressing 100 may increase the distance that wound dressing 100 stretches along the length (L) dimension per unit of stretching force applied along the length (L) dimension. In other words, fenestrations 132 aligned with the width (W) dimension of wound dressing 100 may reduce the stretching resistance of wound dressing 100 along the length (L) dimension. Fenestrations 132 can be spaced uniformly or non-uniformly, as previously described.

Figure 11A:
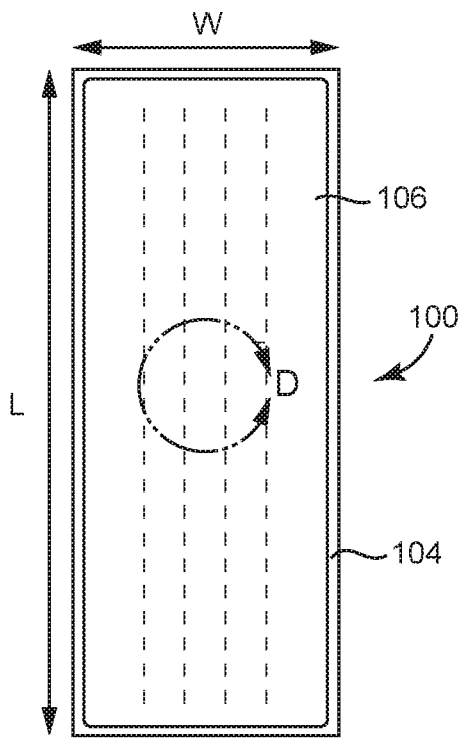
FIG. 11A is a top plan view of the wound dressing of FIG. 1 showing a plurality of fenestrations aligned with a length dimension of the wound dressing without the plurality of welds, according to an exemplary embodiment.
Figure 11B:
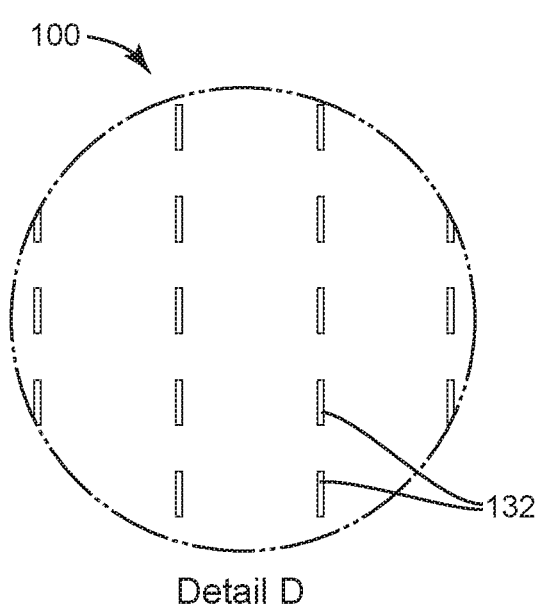
FIG. 11B is a detail view of a portion of FIG. 11A, according to an exemplary embodiment.

FIGS. 11A-11B illustrate an embodiment in which wound dressing 100 includes several columns of substantially linear fenestrations 132 aligned with the length (L) dimension of wound dressing 100, but does not include any welds 110. Each column of fenestrations 132 may include multiple fenestrations 132 arranged substantially linearly. Fenestrations 132 aligned with the length (L) dimension of wound dressing 100 may increase the distance that wound dressing 100 stretches along the width (W) dimension per unit of stretching force applied along the width (W) dimension. In other words, fenestrations 132 aligned with the length (L) dimension of wound dressing 100 may reduce the stretching resistance of wound dressing 100 along the width (W) dimension. Fenestrations 132 can be spaced uniformly or non-uniformly, as previously described.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A wound dressing comprising:
   an absorbent layer configured to absorb wound fluid and having a first side and a second, wound-facing side;
   an elastic film configured to elastically stretch when a stretching force is applied to the wound dressing and elastically recover when the stretching force is removed;
   a plurality of welds that fix the elastic film to the first side of the absorbent layer such that the elastic film and the absorbent layer elastically stretch and elastically recover as a unit; and
   a plurality of linear fenestrations disposed through at least one of the elastic film or the absorbent layer and positioned between the plurality of welds.

2. The wound dressing of claim 1, wherein the elastic film is configured to apply an elastic recovery force to the absorbent layer via the plurality of welds when the stretching force is removed, the elastic recovery force causing the absorbent layer to elastically recover.

3. The wound dressing of claim 1, wherein the absorbent layer comprises a nonwoven hydrofiber material.

4. The wound dressing of claim 1, wherein the absorbent layer comprises an entanglement of nonwoven fibers configured to separate from each other when the stretching force is applied.

5. The wound dressing of claim 1, wherein the absorbent layer comprises a plurality of cellulosic gelling fibers comprising at least one of carboxymethyl cellulose, carboxylethyl cellulose, hydroxyethyl cellulose, hydroxypropyl cellulose, hydroxypropylmethyl cellulose, or cellulose ethyl sulphonate.

6. The wound dressing of claim 1, wherein the absorbent layer comprises a plurality of reinforcing fibers comprising at least one of a polyurethane gel, an amide polymer, an olefin polymer, an ester polymer, or a modified acrylamide polymer.

7. The wound dressing of claim 1, wherein the absorbent layer comprises a plurality of cellulosic gelling fibers and a plurality of reinforcing fibers.

8. The wound dressing of claim 7, wherein:
   the plurality of cellulosic gelling fibers form between 45% and 90% of the absorbent layer; and
   the plurality of reinforcing fibers form between 10% and 55% of the absorbent layer.

9. The wound dressing of claim 1, wherein the elastic film has a thickness between 20 microns and 50 microns.

10. The wound dressing of claim 1, wherein the plurality of welds are distributed non-uniformly such that the plurality of welds cause the wound dressing to elastically stretch and elastically recover non-uniformly.

11. The wound dressing of claim 1, further comprising a backing layer adhered to the elastic film layer opposite the absorbent layer.

12. The wound dressing of claim 11, wherein the backing layer is substantially impermeable to liquid and substantially permeable to vapor.

13. The wound dressing of claim 11, wherein the backing layer extends beyond a perimeter of the elastic film and the absorbent layer to provide an adhesive-coated margin configured to adhere the wound dressing to a surface.

14. The wound dressing of claim 1, further comprising a non-adherent layer coupled to the second, wound-facing side of the absorbent layer.

15. The wound dressing of claim 14, wherein the non-adherent layer comprises a hydrophobic material.

16. The wound dressing of claim 14, wherein the non-adherent layer comprises at least one of an alkyl acrylate polymer, an alkacrylate polymer, or an alkyl alkacrylate polymer.

17. The wound dressing of claim 14, wherein the non-adherent layer comprises a plurality of perforations distributed across a surface of the non-adherent layer.

18. The wound dressing of claim 1, wherein the plurality of fenestrations are configured to increase a distance that the wound dressing stretches per unit of the stretching force.

19. The wound dressing of claim 18, wherein the plurality of fenestrations are distributed non-uniformly such that the plurality of fenestrations cause the wound dressing to elastically stretch and elastically recover non-uniformly.

20. The wound dressing of claim 1, wherein the wound dressing comprises: a length defining a size of the wound dressing along a first dimension; and a width less than the length and defining a size of the wound dressing along a second dimension substantially perpendicular to the first dimension.

21. The wound dressing of claim 20, wherein the plurality of linear fenestrations are aligned with the first dimension or the second dimension.

22. The wound dressing of claim 21, wherein the plurality of fenestrations are aligned with the first dimension and configured to increase a distance that the wound dressing stretches per unit of the stretching force when the stretching force is applied along the second dimension.

23. The wound dressing of claim 21, wherein the plurality of fenestrations are aligned with the second dimension and configured to increase a distance that the wound dressing stretches per unit of the stretching force when the stretching force is applied along the first dimension.

* * * * *